US008781987B1

(12) United States Patent
Shuster et al.

(10) Patent No.: US 8,781,987 B1
(45) Date of Patent: Jul. 15, 2014

(54) DECISION MAKING USING ALGORITHMIC OR PROGRAMMATIC ANALYSIS

(71) Applicants: Gary Stephen Shuster, Fresno, CA (US); David Goldsmith, Manlius, NY (US)

(72) Inventors: Gary Stephen Shuster, Fresno, CA (US); David Goldsmith, Manlius, NY (US)

(*) Notice: Subject to any disclaimer, the term of this patent is extended or adjusted under 35 U.S.C. 154(b) by 0 days.

(21) Appl. No.: 14/142,356

(22) Filed: Dec. 27, 2013

Related U.S. Application Data

(60) Provisional application No. 61/747,992, filed on Dec. 31, 2012, provisional application No. 61/790,864, filed on Mar. 15, 2013.

(51) Int. Cl.
G06F 17/00 (2006.01)
G06N 5/02 (2006.01)

(52) U.S. Cl.
USPC .......................................................... 706/46

(58) Field of Classification Search
None
See application file for complete search history.

(56) References Cited

U.S. PATENT DOCUMENTS

| 4,489,387 | A | 12/1984 | Lamb et al. | |
|---|---|---|---|---|
| 6,741,975 | B1* | 5/2004 | Nakisa et al. | 706/47 |
| 2006/0010443 | A1 | 1/2006 | Lahti et al. | |
| 2007/0011105 | A1* | 1/2007 | Benson et al. | 706/1 |
| 2007/0011106 | A1* | 1/2007 | Benson et al. | 706/1 |
| 2007/0011108 | A1* | 1/2007 | Benson et al. | 706/8 |
| 2008/0249804 | A1 | 10/2008 | Kim | |
| 2011/0173147 | A1* | 7/2011 | de Kleer et al. | 706/46 |
| 2012/0078831 | A1 | 3/2012 | Newcott | |
| 2012/0150782 | A1* | 6/2012 | Benson et al. | 706/45 |
| 2012/0317102 | A1* | 12/2012 | Hu et al. | 707/723 |
| 2014/0006336 | A1* | 1/2014 | Khan et al. | 706/52 |

FOREIGN PATENT DOCUMENTS

| JP | 2006-059325 | 3/2006 |
|---|---|---|
| JP | 2010-146417 | 7/2010 |
| KR | 10-0538582 | 12/2005 |

OTHER PUBLICATIONS

"Research on Repository and Reasoning mechanism of military equipment support resources units location Decision-making support system" Wang et al © 2008 IEEE.*
"Credo: a Military Decision-Support System based on Credal Networks" Antonucci et al 16th International Conference on Information Fusion Istanbul, Turkey, Jul. 9-12, 2013.*
International Search Report and Written Opinion in regard to PCT/US2013/078091 date Apr. 28, 2014 in 9 pages.

* cited by examiner

Primary Examiner — Kakali Chaki
Assistant Examiner — Luis Sitiriche
(74) Attorney, Agent, or Firm — Knobbe Martens Olson & Bear LLP

(57) ABSTRACT

A system for determining an instruction in a first time limit that can be executed by an executing system is disclosed. The system is configured to request proposed action regarding an event from each of a plurality of operator systems. In some embodiments, the system can calculate a score for each of the proposed actions received from the plurality of operator systems. The system can then automatically determine an instruction in a first time limit based on the calculated scored and command the executing system to execute the instruction.

20 Claims, 9 Drawing Sheets

EVENT LOG

Event 1
Request: Fire a missile on the target shown?
Request Time: 10h:40m:00s
Threshold Cutoff Score: 50

| Operator | Response | Response Received | Score |
|---|---|---|---|
| Operator 1 | Yes | 10h:40m:30s | 20 |
| Operator 2 | No | 10h:40m:20s | 30 |
| Operator 3 | No | 10h:40m:50s | 60 |
| Operator 4 | No | 10h:41m:30s | 70 |

Instruction Sent: No
Time of Decision: 10h:41m:00s
Decision Time: 60 seconds Notes:
Operator 4 decision not taken into account because of the lag.

FIG. 8

DECISION MAKING USING ALGORITHMIC OR PROGRAMMATIC ANALYSIS

CROSS-REFERENCE TO PRIORITY APPLICATIONS

This application claims priority under 35 U.S.C. §119(e) to U.S. Provisional Patent Application No. 61/747,992, filed Dec. 31, 2012, and titled "DECISION MAKING USING ALGORITHMIC OR PROGRAMMATIC ANALYSIS," and to U.S. Provisional Patent Application No. 61/790,864, filed Mar. 15, 2013, and titled "DECISION MAKING USING ALGORITHMIC OR PROGRAMMATIC ANALYSIS" the entirety of which are hereby incorporated by reference and made a part of this specification for all that it discloses.

BACKGROUND

Strategies are typically developed by a plurality of decision makers. However, in nearly all cases the final decision may be left to a single individual. For example, an operator of an unmanned aerial vehicle or drone may be acting upon general instructions determined at a meeting of numerous decision makers, but ultimately the operator is left with the final decision by virtue of being the person charged with actually executing the decision. If the operator is provided with instructions to do action A when the operator observes condition B, it is the operator, and not those who provided the instructions, charged with determining when condition B exists and when to do action A.

SUMMARY

The systems and methods described herein can be implemented by a computer system comprising computer hardware. The computer system may include one or more physical computing devices, which may be geographically dispersed or co-located.

Certain aspects, advantages and novel features of the inventions are described herein. It is to be understood that not necessarily all such advantages may be achieved in accordance with any particular embodiment of the inventions disclosed herein. Thus, the inventions disclosed herein may be embodied or carried out in a manner that achieves or selects one advantage or group of advantages as taught herein without necessarily achieving other advantages as may be taught or suggested herein.

In certain embodiments, a system for generating instructions to execute from an executing system can include one or more hardware processors configured to execute a plurality of software modules.

In one embodiment, a computer-implemented system for determining an instruction in a first time limit that can be executed by an executing system comprises one or more computer processors and a non-transitory computer-readable storage device storing instructions configured for execution by one or more computer processors in order to cause the system to request proposed actions regarding an event from each of a plurality of operator systems, receive proposed actions from the plurality of operator systems, wherein the proposed actions are based at least on data corresponding to an environment associated with the event. In one embodiment, for each operator system the system provides a proposed action, determines a weighting associated with the operator system based on one or more parameters of the operator systems, the parameters comprising one or more of a proximity of the operator system to an execution location, experience of an operator associated with the particular operator system in making decisions regarding other events of a similar type to the event, and calculates a score for each of the proposed actions received from the plurality of operator systems based on the respective determined weightings associated with the operator systems, determine an instruction in a first time limit based on the calculated scores for each of the proposed actions received from the plurality of operator systems, said instruction configured to be executed by an executing system. The system may further command the executing system to execute the instruction within the first time limit that is based at least on one of the proposed actions received from the operator systems.

In one embodiment, the instruction to calculate a score for each of the proposed actions received from the plurality of operator systems comprises simulate results for each of the proposed actions, and calculate a score based on the simulated results. In one embodiment, the instructions are further configured to cause the system to select plurality of operator systems based on one or more parameters of the operator systems, the parameters comprising one or more of a proximity of the operator system to an execution location, experience of an operator associated with the particular operator system in making decisions regarding other events of a similar type to the event. In one embodiment, the first time limit comprises real time. In one embodiment, the first time limit comprises less than or equal to one minute. In one embodiment, the environment associated with the event includes an operating room environment, said data corresponding to the environment associated with the event including patient data. In one embodiment, the environment associated with the event includes a securities transaction environment, said data corresponding to the environment associated with the event including stock market data. In one embodiment, the environment associated with the event includes a military environment, said data corresponding to the environment associated with the event including field data. In one embodiment, the environment associated with the event includes a military environment, said data corresponding to the environment associated with the event including field data from a system on the field. In one embodiment, the environment associated with the event includes a factory environment, said data corresponding to the environment associated with the event including machine data.

In one embodiment, a method of determining an instruction in a first time limit that can be executed by an executing system comprises requesting proposed actions regarding an event from each of a plurality of operator systems, receiving proposed actions from the plurality of operator systems, wherein the proposed actions are based at least on data corresponding to an environment associated with the event, for each operator system providing a proposed action, determining a weighting associated with the operator system based on one or more parameters of the operator systems, the parameters comprising one or more of a proximity of the operator system to an execution location, experience of an operator associated with the particular operator system in making decisions regarding other events of a similar type to the event, calculating, using one or more hardware processors, a score for each of the proposed actions received from the plurality of operator systems based on the respective determined weightings associated with the operator systems, determining an instruction in a first time limit based on the calculated scores for each of the proposed actions received from the plurality of operator systems, said instruction configured to be executed by an executing system, and commanding the executing system to execute the instruction within the first time limit that is based at least on one of the proposed actions received from the operator systems.

In one embodiment, the calculating a score for each of the proposed actions received from the plurality of operator systems comprises simulating results, using one or more hardware processors, for each of the proposed actions, and calculating, using one or more hardware processors, a score based on the simulated results. In one embodiment, selecting a plurality of operator systems based on one or more parameters of the operator systems, the parameters comprising one or more of a proximity of the operator system to an execution location, experience of an operator associated with the particular operator system in making decisions regarding other events of a similar type to the event. In one embodiment, the first time limit comprises real time. In one embodiment, the first time limit comprises less than or equal to one minute. In one embodiment, the environment associated with the event includes an operating room environment, said data corresponding to the environment associated with the event including patient data. In one embodiment, the environment associated with the event includes a securities transaction environment, said data corresponding to the environment associated with the event including stock market data. In one embodiment, the environment associated with the event includes a military environment, said data corresponding to the environment associated with the event including field data. In one embodiment, the environment associated with the event includes a military environment, said data corresponding to the environment associated with the event including field data from a system on the field. In one embodiment, the environment associated with the event includes a factory environment, said data corresponding to the environment associated with the event including machine data.

BRIEF DESCRIPTION OF THE DRAWINGS

Embodiments disclosed herein are described below with reference to the drawings. Throughout the drawings, reference numbers are re-used to indicate correspondence between referenced elements. The drawings are provided to illustrate embodiments of the inventions described herein and not to limit the scope thereof.

FIG. 8 illustrates an example user interface that includes information regarding a decision request, including responses received from various operators.

DETAILED DESCRIPTION

I. Introduction

Critical decision making is involved in almost every discipline such as military, surgical, securities, factory plant operations, etc. Human error can be a persistent problem when it comes to making decisions and the problem might be even more amplified while making critical decisions in stressful situations. When people evaluate data, they frequently make erroneous determinations and as a result take incorrect actions. Sometimes, people are affected by bias while at other times it may be because they do not have access to all the data. Similarly, computer systems designed to process real world data and recommend or take actions can also be prone to errors. While computer systems do not suffer from bias, they may suffer from lack of human empathy, lack of available data, and experience.

This disclosure describes embodiments of decision generator systems that can automatically generate instructions based on a plurality of inputs. A decision generator system can assist in a military setting, for example, by sending instructions to a field executing system (such as an unmanned aerial vehicle (UAV)) based on a plurality of inputs, including proposed actions from one or more operators. For example, the decision generator system can receive input from a first UAV operator to fire a missile on a target and a second input from a second UAV operator to not fire a missile on the target. The decision generator system can receive (e.g., intercept) both the proposed actions, determine a final instruction and send the instructions directly to the UAV. In the above example, the decision generator can lower the weighting of the proposed action from the second operator based on a determination that the second operator is located remotely as compared to first operator who is on the field. The decision generator system can also take into account whether it would make more sense to wait to fire a missile depending on the current weather data. As can be evident from the above example, decisions may be critical and need to be made in a time limit including real time (that is, in a window of seconds or minutes). Decision generator systems can intercept several proposed actions, take into account background data (including operator background data, situation background data, field data, etc.), and directly interface with the decision executing system to execute a decision within a tight timeline. Thus, decision generator systems can improve decision making ability of real world systems.

Figure 1:
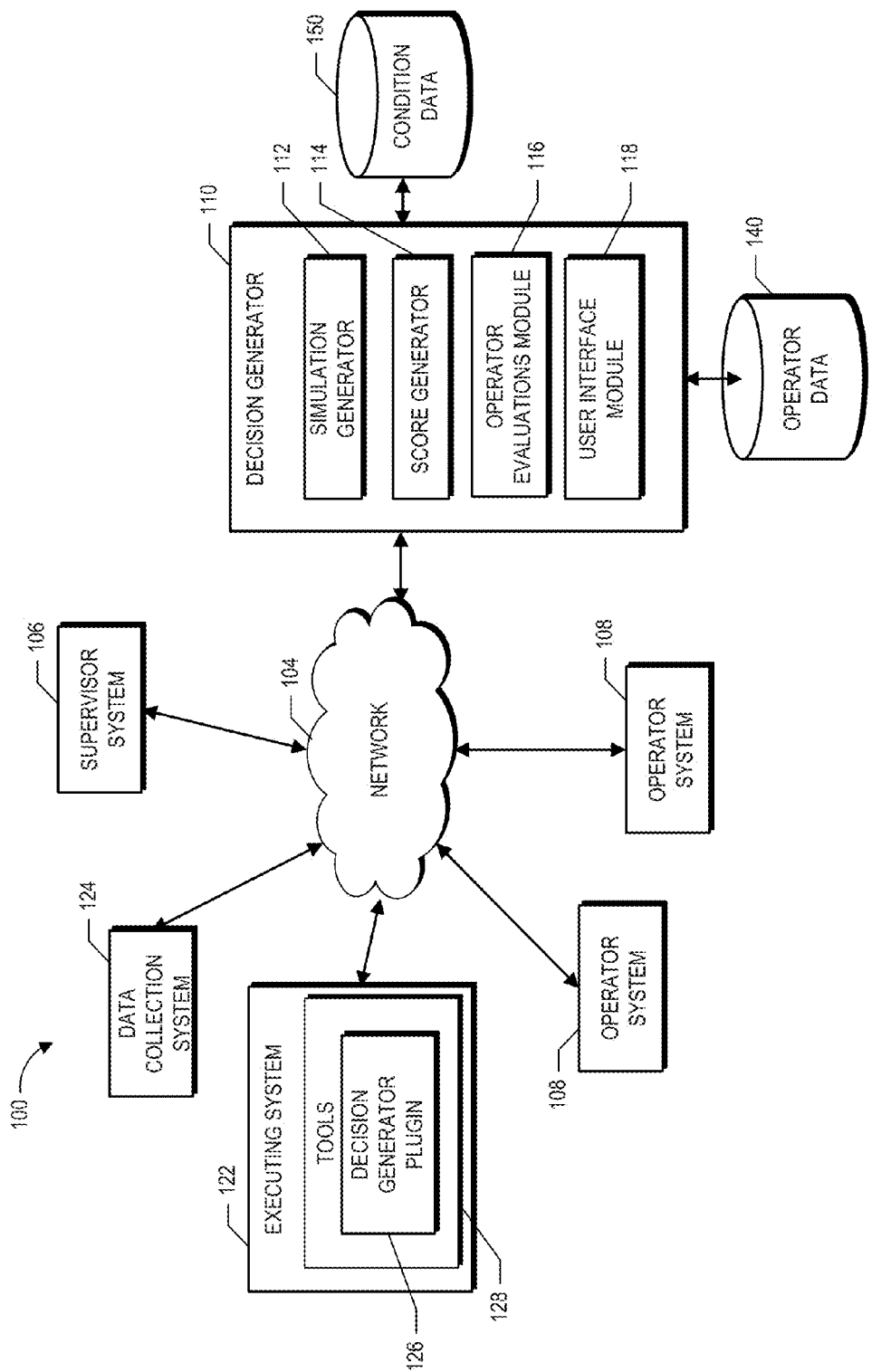
FIG. 1 illustrates an embodiment of a computing environment including a decision generator system that can automatically generate instructions for execution from an executing system based on plurality of inputs.

The features of the systems and methods described herein can also be implemented to generate instructions in a non-military environment. For example, decision generator systems can be used in operating rooms of hospitals, securities transactions, factory operations, and in other operations where there is need to reduce human error. Thus, decision generator systems can aggregate, score, and/or analyze data from a plurality of inputs, whether human, computer, live, historical, or a combination, in order to improve accuracy in decision making II. Example Decision Generator System FIG. 1 illustrates an embodiment of a computing environment 100 including a decision generator system 110 that can receive inputs indicating proposed actions, generate instructions based on the received proposed actions, and send instructions to one or more executing systems 122 for execution.

In general, the operator systems 108 can include any type of computing device capable of executing one or more applications and/or accessing network resources. For example, the operator systems 108 can be desktops, laptops, netbooks, tablet computers, smartphones, PDAs (personal digital assistants), servers, smartwatches, augmented-reality wear, e-book readers, video game platforms, television set-top boxes (or simply a television with computing capability), a kiosk, combinations of the same, or the like. The operator systems 108 include software and/or hardware 132 for accessing the decision generator system 110, such as a browser or other client software (including an "app"). Human operators can use the operator systems 108 to receive data relating to a decision and accordingly select or enter proposed actions. In some embodiments, the operator systems 108 can be automated and capable of sending proposed action without human intervention.

Supervisor systems 106 can also include any type of computing device capable of executing one or more applications and/or accessing network resource described above. In some instances, the decision generator system 110 may send proposed actions from the operator systems 108 to the supervisor system 106 for review. For example, when all the proposed actions fall below cut-off point for executing an instruction automatically (e.g., without human intervention), the decision generator system may need approval from a supervisor system 106 before sending instructions to executing systems 122.

Executing systems 122 can also include any type of device or a group of devices capable of receiving instructions and executing a command. For example, executing systems 122 can include unmanned aerial vehicles (UAV), surgical instruments (e.g. Intuitive Surgical's® daVinci Surgical System), factory operation system, securities transaction system, space station system, computer assisted drive vehicles, trains, planes, etc. In some embodiments, executing system 122 can include any type of computing device capable of executing one or more applications and/or accessing network resources.

Data collecting (or collector) systems 124 can include any type of device or a group of devices capable of gathering environment or condition data. In some embodiments, data collector systems 124 may operate with limited or no human intervention. For example, data collecting system 124 can include satellites, field robots, patient monitoring systems, data servers etc. In some embodiments, data collecting system 124 can include any type of computing device capable of executing one or more applications and/or accessing network resources. Data collecting system 124 can also include executing systems 122.

The executing system 122 includes one or more tools 128, such as proprietary software for operating an executing system, such as a UAV or a surgical instrument. In some embodiments, the decision generator system 110 can be integrated with the tools through a plug-in 126 or an API (application programming interface). The tools may come pre-installed with a plug-in to the decision generator system 110. In other embodiments, a plugin to the decision generator system 110 may be installed on to the tools 128.

The decision generator system 110 can be implemented in computer hardware and/or software. The decision generator system 110 can execute on one or more computing devices, such as one or more physical server computers. In implementations where the mobile safety system 110 is implemented on multiple servers, these servers can be co-located or can be geographically separate (such as in separate data centers). In addition, the decision generator system 110 can be implemented in one or more virtual machines that execute on a physical server or group of servers. Further, the decision generator system 110 can be hosted in a cloud computing environment, such as in the Amazon Web Services (AWS) Elastic Computer Cloud (EC2) or the Microsoft® Windows® Azure Platform. Aspects of the decision generator system 110 can also be implemented in hardware and/or software on the executing systems 122.

The decision generator system 110 can include, one or more modules, to generate a decision or instructions for the executing system 122. For example, the decision generator system 110 can include a score generator module 114 that can score proposed actions from various operator systems 108 according to various criteria described herein. In an embodiment, the score generator module 114 can receive inputs from an operator evaluation module 116 that can evaluate an operator based on their background, previous track records, or access to relevant data, for example. The score generator module 114 can also review simulation results generated by simulation generator module 112 in calculating proposed action scores. The score generator module 114 can determine instructions based on scoring proposed actions. In an embodiment, the score generator module 114 can select the highest scoring action exceeding a cut-off point. Based on the calculations described more in detail below, the score generator module 114 can send final instructions to the executing system 122.

Executing systems 122 can include a decision generator system 110 plug-in or may access the decision generator system 110 over a network. The decision generator system 110 plug-in can include all or some of the following modules: simulation generator 112, score generator 114, operator evaluations module 116, and user interface module 118. The operator systems 108 can remotely access the decision generator system 110 through the network 104, which may include one or more local area network (LAN), wide area network (WAN), such as the Internet, combinations of the same, or the like. For example, the network 104 can include an organization's private intranet, the public Internet, or a combination of the same. The operator systems 108 can include thick or thin client software that can access the decision generator system 110 via the network 104. In some embodiments, operator software on the operator system 108 can be a browser software or other application software. The operator system 108 can access the decision generator system 110 through the browser software. In certain embodiments, some or all functionality of the decision generator system 110's can be implemented on the operator systems 108. The computing environment 100 can also include data repositories 140 and 150 for storing operator and condition data, respectively. Operator data can include information regarding particular operators, such as information that may be useful in determining or updating weightings assigned to operator systems 108. For example, operator data may include, for each of multiple operators, the operator's success rating, operator's personal biographical information, among other information. Condition data can include any data related to a request decision that may be useful in determining the appropriate instructions for an executing system. For example, condition data can include environmental data, such as weather information at or around the event location and/or at or around the location of an operator (e.g., if the operator is offsite from the event location), information regarding financial data history, such as stock exchange index history financial application or patient medical history in a medical decision application, or any other information.

III. Example Decision Generator System in a Military Environment

Figure 2:
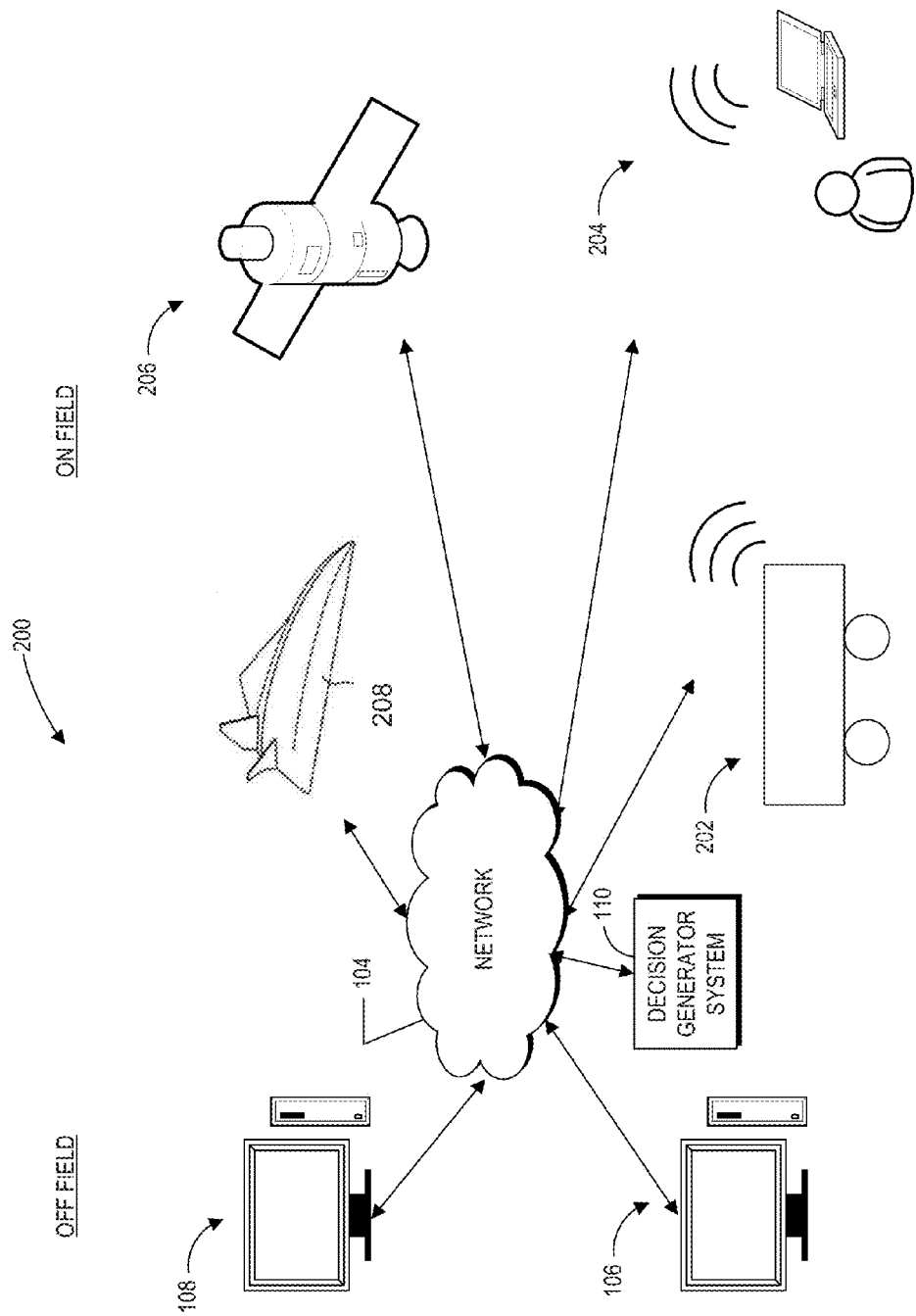
FIG. 2 illustrates a military environment where an embodiment of a decision generator system can be used to generate field decisions.

FIG. 2 illustrates an embodiment of a decision generator system 110 that can operate in a military environment 200. The military environment 200 can include devices both on and off-field. On-field devices can include executing system (e.g. UAV as depicted) 208 that can execute commands such as fire a missile on a target. The decision generator system 110 can send instructions to the UAV 208 based on proposed actions received from off-field operator system 108 and/or supervisor systems 106 and/or field operator systems 204. In an embodiment, some or all of the components of the decision generator system 110 can be implemented in the executing system (UAV) 208. The decision generator system 110 can also receive additional data from data collecting systems 124 including satellites 206 that may collect weather data, GPS, or field images. In addition, the decision generator system 110 can receive data from field operatives that may be on the field transmitting data through a computing device 204. The decision generator system 110 can also receive data from robotic devices 202. As evident from the disclosure above, the decision generator system 110 can be used in any environment where a plurality of decision makers are making a decision based on a plurality of inputs from multiple systems. The decision generator system 110 can receive data from a plurality of sources through the network 104 as describe above with respect to FIG. 1.

Taking as an example a control center for unmanned aerial vehicles armed with missiles, there may be a plurality of such vehicles controlled by a like number of persons or by a number of persons less than the number of vehicles (e.g., one person may be responsible for more than one vehicle, or a team of people may split control of a group of vehicles, such as a system where a vehicle that requires attention is assigned on the spot to a single operator). There may also be computer analysis of inbound data which may be presented to operators in order to aid in their control of the vehicles. The people and computers providing data about the decision and control inputs to the vehicles will have different levels of experience, different track records with regard to past decisions, different decision making speeds and methodologies, and vary in other ways. There is currently no way to fully leverage the expertise and information from all of the inputs in order to minimize the risk of error, particularly in real time. While UAVs are disclosed as an example, the disclosure is not limited to vehicle control, and indeed may be used in a variety of application, such as in surgical settings or in corporate decision making.

In one aspect, the decision generator system may utilize inputs from N operators using operator systems 108. Each input may then be provided a weighting according to certain relevant data with regard to the decision at hand, such as characteristics of the operator providing the proposed decision (expertise, rank, past performance, decision making speed, decision making accuracy within time constraints similar to those at hand), characteristics of the computer systems involved in obtaining reference data and/or providing the proposed decision to the decision generator system (e.g., latency in communications, sensor accuracy, processor speed), characteristics of an environment of the operator (e.g., location of operator, weather conditions, amount of light, etc.), and/or other factors that may indicate proposed decisions of an operator are more or less valuable than those of other operators. In one example, an operator associated with operator system N1 may have a score of 20, N2 may have a score of 25, and N3 may have a score of 30, based on some combination of the characteristics noted above and/or other related characteristics. These may be determined as raw numbers with a weight attached to the number, as a percentage, or using any other scale.

As noted above, results of past decision making history of particular operators in similar situations (or all, recent, or some other grouping of situations) may be included in weightings associated with inputs (e.g., proposed actions) received from those operators. Historical analysis may be saved in one of the data repositories 140 or 150. Similarly, cultural or personal information about the operators may be utilized in the weightings. Thus, in some embodiments, weightings may be particular to the decision to be made. For example, an operator may have a very high weighting for a first type of decision (e.g., whether to fire a missile at a location very near to a civilian area), but a low weighting for a second type of decision (e.g., whether to use a particular interrogation technique on a detainee). As an example, an input from an operator born in Kabul may be given a lower score (e.g., based on a low weighting) in a decision whether to fire a missile toward the neighborhood of his birth. Similarly, an operator with a young child may have his score altered (e.g., by adjusting the weighting associated with the operator) based on the likelihood that children will be impacted by a certain decision.

In one embodiment, a bias toward or against a certain action may be built into the decision logic used by the decision generator system based on a situation's overall characteristics. For example, any drone flying over friendly territory may be controlled by a mechanism that overweights input rejecting a missile-launch decision. Such weighting may change based on the extent political environment, the visibility or weather, or other factors. Where the availability of information to operators is not uniform, such as where some operators have access to classified documents but others do not, those with more information may be given a different weighting. Where some decisions may reveal classified information (such as a decision to target a schoolhouse based on information that it is not used as a school, but as a laboratory), the outcome of the decision making process may be hidden from certain participants (for example, operators or some supervisors), and in some cases a simulation of a different decision may be presented to certain participants (such as, in the schoolhouse example, simulated video of the drone overflying the schoolhouse without launching). Where classified information is at issue, the system may also select participants based, in whole or part, on access to such information and/or clearance to receive such information. As an example, operators N1, N2, N3, and N4 may have clearance levels 1, 2, 3, and 4, respectively and supervisors S1 and S2 may have clearance levels 2 and 4, respectively. Certain decisions may require access to data only available to participants with clearance level 3 or higher. Accordingly, in some embodiments, the decision generator system 110 may only select operators N3 and N4 and supervisor S2 to send a request for proposed actions.

The process may be iterative, in that a lower level decision process may have an outcome or a set of recommended actions and score (e.g., based on proposed actions provided by a first set of operators) that is then sent to a higher level for approval or modification (e.g., based on proposed actions provided by a second set of operators, which may be entirely different than the first set of operators). For example, input from multiple lower level operators may first be received and analyzed in order to determine a recommendation and then, in response to the recommendation having a particular value (e.g., the recommendation may indicate that a missile strike should be performed), the same decision may be presented to higher-level operators, possibly in conjunction with the recommendation based on inputs from the lower level operators, in soliciting proposed actions from those higher-level operators which may be analyzed by the decision generator system in order to make the final recommendation, which may then be automatically executed by one or more executing systems 122. In this example, if the initial recommendation based on inputs from the lower level operators does not have the particular value (e.g., the recommendation indicates that a missile strike should not be performed), the same decision may not be presented to the higher level operators. In some embodiments, multiple layers of decision inputs are solicited from groups of operators in order to reach a final recommendation for execution by an execution system. In one embodiment, a higher level process, such as one that incorporates overall geopolitical strategy, may be executed in order to select between similarly weighted recommendations.

When a decision point exists, data can be provided to a plurality of decision makers (operators using operator systems 108, supervisors using supervisor systems 106, etc.) and each of their recommended decisions can be converted to a weighted score. In one embodiment, taking a decision to fire a missile, a raw score of 50 may be required in order to provide a recommendation that is automatically executed (e.g., without further human intervention), in which case the missile could not be fired without N3 agreeing. Depending on the embodiment, the raw score of each of the operators providing a proposed action may be combined in order to determine whether or not a threshold is reached. For example, in one embodiment each of the raw scores of operators providing proposed actions (or only those operators providing a particular proposed action in one embodiment) are aggregated, such as by adding, averaging, or combining in some other statistical manner. Thus, in example noted above where N1 had a score of 20, N2 had a score of 25, and N3 had a score of 30, a combined score for the three operators may be 75 in an embodiment where the scores are all summed or 25 in an embodiment where the scores are averaged. Assume that N2 provided a different proposed action than N1 and N3. In this example, the contrary recommendation may be used to reduce the aggregate score. For example, if N1 and N3 each provide a proposed action of firing on the indicated target, their combined score would be 50, but N2's disagreement may then reduce the total score to +25 to fire (20+30−25), which may then be an aggregate score that is not high enough to reach the cutoff threshold for providing the "fire" recommendation (or may not be sufficient to provide such a recommendation for automatic completion, but may still reach a lower threshold to provide the recommendation to a human operator or supervisor that can then make the final determination as to whether the "fire" recommendation should be completed). In some cases, a recommendation to do or not do an action may be weighted more highly than the opposite recommendation. For example, a recommendation not to fire a missile may be weighted as twice the value of a recommendation to fire.

In one aspect, the difference between the scores must be greater than Z % in order to make a decision. For example, if the "yes" value is 80 and the "no" value is 60, and the required difference is 50%, because the difference between 80 and 60 is less than 50%, no decision would be made. In another aspect, a statistical difference (such as one standard deviation) may be required. In another aspect, the raw score may be measured as a percentage or calculation of the total score possible if all decision makers were participating, so that a non-participating recommender may be automatically counted as a "no" or a "yes". In some embodiments, where there are more than two possible decisions, it may be particularly useful to utilize a method whereby a certain raw score or statistical significance may be required, or where one decision may be required to be recommended by a certain margin over all other possible decisions combined. In another aspect, a parallel decision as to whether delay is acceptable, unacceptable, and/or recommended may be made. Such parallel decision may be utilized by itself to determine whether to execute the primary decision, or may be utilized in conjunction with the confidence level in the primary decision to make a determination as to delay. For example, where there is profound disagreement between various operators as to the primary action but general agreement that a delay is acceptable, a delay may be imposed.

In one embodiment, a hierarchal approach to decision making can be used by the decision generator system. For example, the system may follow the hierarchal approach used in the military. For example, the system may provide a higher weight to inputs from those of higher rank, but by automatically incorporating the input of various others in accordance with the disclosures herein, the input of people other than the highest ranking officer can also be incorporated into the decision making process (e.g., with lower weightings). While the armies (and corporations) of decades past may have operated at a speed slow enough to allow higher ranking officers to incorporate advice from others into their decision making process, there are now frequent circumstances where even having a human seeking the input of other humans is effectively impossible. Taking as a non-military example the execution of trading orders, securities are frequently traded to a velocity that makes holding a meeting or similar process impractical. Similarly, the decision to fire a missile from a drone at a target moving from one bunker to another bunker must be made in seconds or fasters, rendering human-to-human consultation impossible. By utilizing the systems and methods described herein, the results of human-to-human meetings may be emulated or approximated, and/or additional input given into the decision, within a timeframe impossible using existing technology.

In light of this and other factors, in another aspect, the speed with which a decision is required may impact the amount of score required to take an action. The determination of the requisite speed may be made using other systems and methods disclosed herein or in another manner.

In another aspect, where a certain threshold is not reached (or, optionally, in all cases), the final decision may need to be approved by another decision maker, by another group of decision makers, by a combination, and/or by some other process.

In some embodiments, the decision generator system 110 can send instructions to the executing system 122 without requiring proposed actions from operators or only requiring a low score. This may depend on the confidence score of available data. Confidence score may be calculated or received from data collecting systems 124. For example, if a computer (executing system 122 and/or data collection system 124) is 100% confident (high confidence score) of its data accuracy, a threshold score of 10 may be required, whereas if the computer is 10% confident of its data accuracy, a threshold score of 100 may be required. Different data may have different confidence scores associated with it. Using the UAV example, a data collecting system (e.g. satellite) 124 may be 100% confident of the GPS coordinates of the missile and the target, but only 80% confidence that the target is a military convoy. In some embodiments, the decision generator system 110 can calculate confidence scores based on characteristics of the data collecting systems 124. For example, the decision generator system 110 can give 100% confidence score for coordinates received from a satellite as compared to 50% confidence score for coordinates received from cell phone triangulation.

In one aspect, one or more operators may provide input that the decision is not urgent and thus should be decided at least in part using some other method. Using the various scoring and evaluation systems described herein, such a decision to delay action may be taken upon meeting certain criteria.

In one aspect, crowdsourcing may be utilized in providing a particular input from an operator system. Relative reputation of people making the inputs may be measured. In another aspect, the technology described in U.S. patent application Ser. No. 12/329,296 ("Anti-Collusive Vote Weighting"), incorporated fully herein by reference, may be utilized to assist in weighting or otherwise scoring the inputs. In one aspect, the crowd-sourced proposed action may be used as an additional input by the decision generator system 110 to determine final instructions.

In another aspect, operators may provide their confidence level in their proposed actions, and this may be used to further refine the weighting of their proposed actions. For example, if N1 has a score of 20 points without considering a self-provided confidence level from N1, if N1 provides an 80% confidence level that the decision should be "yes" N1's score may be reduced to 16 points (e.g., 20 points×0.80=16 points). In another aspect, the confidence (or uncertainty) may be given additional weight or less weight. Correction may be made for bias in scoring, such that scoring is adjusted by the historical distribution (whether in similar cases, all cases, recent cases, and/or according to other criteria) of scores. Thus, for example, if N1 provides a confidence level of 90% a majority of the time, the 90% score from N1 may be adjusted to 45% in an embodiment based on the historical trend indicating that N1's proposed actions are selected only 50% of the time. Other adjustment methodologies may be used as well. In one aspect, the amount of variation in a person's scoring across a plurality of events may be utilized as an indication of reliability and input from that person may be given a higher weight.

IV. Example Decision Generator System in a Surgical Environment

Figure 3:
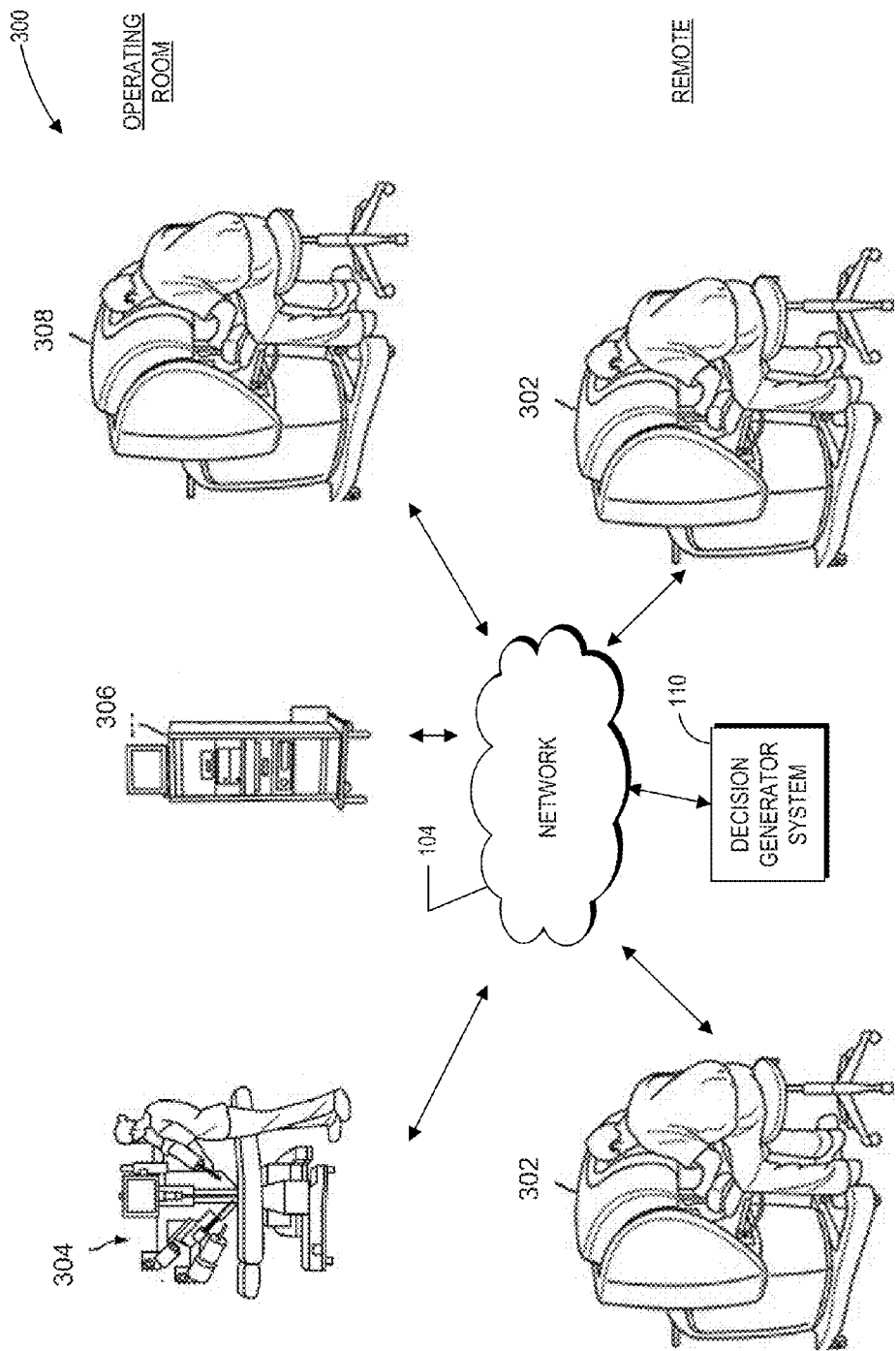
FIG. 3 illustrates a surgical environment where an embodiment of a decision generator system can be used to generate surgical decisions.

FIG. 3 illustrates an embodiment of a decision generator system 110 that can be used in a hospital operating room environment 300 or other similar treatment environment. The hospital environment 300 can include operator systems both in the operating room and remote to the operating room. In-operating room devices can include an executing system 304 (e.g. robotic surgical instrument) that can execute instructions, such as to cut a particular vessel. The decision generator system 110 can send instructions to the surgical instrument 304 based on proposed actions received from one or more remote operator system 302, one or more supervisor systems (not shown), in-operating room operator system 308, and/or other operator system. In one embodiment, medical practitioners with various backgrounds may operate the various operator systems that provide input indicating proposed actions to be performed by the surgical instrument 304. For example, operators that provide input may include one or more surgeons, one or more radiologists, one or more anesthesiologists, one or more insurance representatives, etc., each with respective weightings that determine impact of proposed actions from the respective operators. In this way, input from such various human operators may be combined and processed in real-time (or substantially real-time) to make a decision, wherein such widespread cooperation of multiple operators is not possible otherwise. In an embodiment, some or all of the components of the decision generator system 110 can be implemented in the executing system (surgical instrument) 304. The decision generator system 110 can also receive additional data from patient monitoring systems 306 that may collect patient physiological data (e.g. heart rate, etc.) and stored patient information (e.g. allergies, medications, age, etc), which may also be used in making a decision by the decision generator system 110. For example, if a decision request is provided to multiple operators (such as those medical operators noted above), and the proposed action by the operator is overwhelmingly to perform a particular action (e.g., to perform an epidural on a surgical patient), such proposed action may be overturned (or sent for further review by one or more human operators, potentially including family members of the patient) in view of current patient physiological data or stored patient information. For example, if the stored patient information indicates that the patient had a bad reaction to a previous epidural, the predominant proposed action may be overruled by the decision generator system 110. The decision generator system 110 can receive data from a plurality of sources through the network 104 as describe above with respect to FIG. 1.

In one aspect, machinery or devices may be controlled utilizing a real time (or, in some cases, non-real time) application of the systems described herein to guide decisions on a level as granular as may be helpful. Take as an example surgery done using an executing system similar to the da Vinci® Surgical System. Such a robotic surgery system typically is controlled by a physician or other human, with each instruction to the system being sent by a single person. Indeed, because of a public fear of fully computerized or even computer assisted decision making in the course of a surgery (and/or for other reasons), such surgical systems are implemented in a way that "does not place a robot at the control; [the] surgeon is controlling every aspect of the surgery with the assistance of the da Vinci robotic platform." See, http://www.davincisurgery.com/davinci-surgery/ retrieved Dec. 31, 2012. However, humans make mistakes, and a slip of the hand controlling a surgical robot may be just as damaging as a slip of the hand holding a scalpel. The decision generator systems 110 described herein may be used to improve control of such systems. Although the example here is surgical, other systems may benefit as well. In one aspect, a plurality of operators is provided with real time data from the surgical site, such as video from the surgical site.

Where there is a latency issue, a cut-off for participation (e.g., providing proposed actions that are included in determination of an instruction for the execution system) may be set at an upper limit of latency. In one embodiment, the system may compensate for latency by delaying processing or some other action on inputs received before other inputs so as to treat, as if simultaneously received, inputs from various sources. In another aspect, latency in providing images to the surgeon or other remote operator(s) may be taken into account. For example, in a scenario with three operators, two on-site (and thus with 10 ms latency bidirectionally) and one remote operator (with 110 ms latency in receiving a signal sent to the operator and 210 ms latency in receipt of signals sent by the operator), the total latency for the on-site operators is 20 ms and the total latency for the offsite operator is 320 ms. In one aspect, the system may delay the local input by 300 ms. In another aspect, the system may evaluate whether the additional accuracy provided by utilizing the third, slower participant outweighs the additional advantage to avoiding the 300 ms delay. Such a decision may be made by individual act or motion, by what segment of the procedure is being performed, upon an indication by one or more participants that such condition exists, or in accordance with other inputs or decisions.

Where there are multiple inputs to a procedure, such as a surgery, in one aspect the inputs may be generally characterized by whether they are attempting to make the same movement or kind of movement. For example, where two operators are providing inputs regarding cutting tissue and five operators are providing inputs regarding retracting a vessel, the system may categorize the actions as "retract" and "cut", respectively. It may then determine, according to the methods described herein, which action is to be taken or, if performance of both actions is preferred, an order of the actions (or whether the actions should be taken simultaneously, if possible with the execution system). The decision generator system 110 may utilize data from the operators performing providing inputs regarding such actions as to how such actions should be approached. Using the example further, if the system determines that retraction is the correct action (because it bears the higher score, for example), then input from the five operators attempting retraction may be viewed. In one implementation, the actions of all five operators may be averaged. In another implementation, the median action may be utilized. In another implementation, there may be a primary operator and the actions of the other operators would serve, in whole or part, to stop the primary operator when the actions of the primary operator are more than some threshold varied from the actions of the other operators. Returning to the example, in one implementation, if two of the five operators attempted to grab the vessel at 1 mm from a set point, two of the operators at 2 mm from a set point, and one of the operators at 4 mm from a set point, the high and low may be discarded (so a 1 mm and the 4 mm) and the remaining inputs averaged, with the vessel grabbed at [(1+2+2)/3] mm from the set point.

V. Simulations, Signal Latency, and Additional Data Inputs

In surgical, military, business or other settings, it may be desirable to refine decision making (whether refining the analysis of inputs, adjusting the decision, or making the decision via computer) by running one or more real time simulations of proposed actions or potential decisions. While simulations are discussed, they may also take the form of analysis of database information about similar actions and their results. Returning to the surgical example, the simulation may indicate that retracting the vessel without first cutting the tissue would likely result in a tear in the tissue, and may thus determine that the input from the operators attempting to cut the tissue should take priority. In another aspect, the decision generator system may analyze whether the risk of delay is greater than the risk of not having the operators make the decision, and may in some cases not execute any of the proposed actions, but instead present the issue to a different group of operators.

In a military example, where a drone is attempting to strike down an enemy aircraft with a missile, the real time simulation may be used as the sole input, or as an additional input, in determining whether a proposed action is likely to succeed. If, for example, three operators each provide input indicating targeting of the missile at slightly different angles, the system may determine that simulated results indicate that operator 1's action is 50% likely to hit, operator 2's action is 80% likely to hit, and operator 3's action is 90% likely to hit. Such scores may be used in weighing which action to adopt. If, taking the example further, operator 2 has 100 points and operators 1 and 3 each have 25 points, and the simulation is assigned one point per percentage likelihood of success, the proposed action of operator 1 would have 75 points (50 points from the simulation and 25 points from the operator), the proposed action of operator 2 would have 180 points (80 points from the simulation and 100 points from the operator), operator 3 would have 115 points (90 points from the simulation and 25 points from the operator). Thus, the decision generator system may determine that the proposed action from operator 2 is utilized (or, in the case of input averaging, provided greater weight). Cutoff points may be set so that a very low or very high chance of success in a simulation may increase the weighting providing to the simulation for the operator with such score.

In some cases with operators in multiple locations, the issue of signal latency may be significant and may be dealt with in the manner described above. However, in some cases there may also be decision making latency. That is, some people (or computers) react more quickly than others. In selecting which operators to send requests for proposed actions for a particular decision event, such latency may be taken into account. In addition, deviation from normal latency may be utilized to adjust weighting of scores (if, for example, an operator who usually takes 2000 ms to decide in this case takes 6000 ms, that may be an indication that the operator has done more analysis than normal). Similarly, operator latency may be compensated for by taking the normal latency period for the various operators in such situations and treating it as if it were added to the communications latency. Such overall latency may then be dealt with as described above. The latency issue may be present in a variety of situations, and is not limited to surgical or similar applications.

Multiple decision requests relating to the same event may be sent by the decision generator system 110 to different group of operators for increasing speed of decision making. For example, a first group of operators may answer "Will a rail gun be effective against the target?" and a second group operators may answer "Is this the target that we want to hit?" Operators may be selected based on their expertise and/or other factors, such as those discussed above. Additional data inputs may also be utilized, as described in U.S. provisional patent application 61/747,348 filed Dec. 30, 2012 and titled "Situational and global context aware calendar, communications, meeting, and relationship management", the entirety of which is incorporated herein as if set forth in full. Data relevant to the decision may, in certain cases, include sources that are non-public and in some cases classified, such as certain satellite data.

Where there is time pressure, the threshold number of participants (or points towards a particular proposed action) needed before an instruction may be determined and/or provided to an execution system may be reduced. In another aspect, a set number of 100% confidence level recommendations, or a threshold amount/percentage of 100% confidence level recommendations, optionally where the recommendations are all identical, may be used to determine a course of action even where the score for that recommendation may otherwise be inadequate to result in the proposed action being implemented in an instruction to the execution system.

In another aspect, as a decision reaches a point of no return (for example, the point at which a missile can no longer be diverted away the target), the value assessed to "no" votes may be increased. This may be done generally, in the presence of new information (such as video from the missile tip), or in a combination of such circumstances. In some implementations, even a single "no" recommendation may be enough to abort the action where significant new data has arrived in the intervening period, or a plurality of "no" votes may be required.

VI. Example Decision Generator User Interfaces

Figure 4:
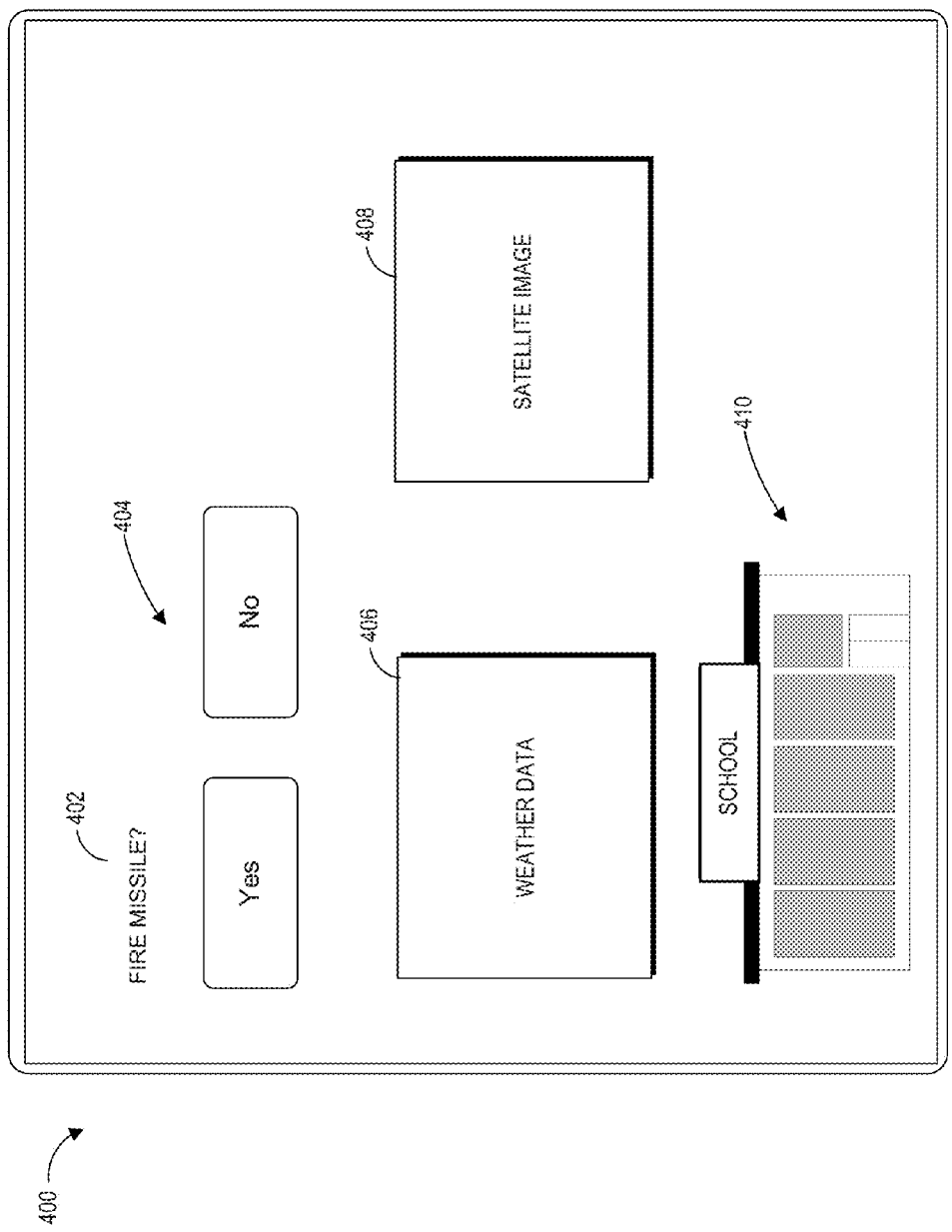
FIG. 4 illustrates an embodiment of a user interface for receiving proposed actions in a military environment.
Figure 5:
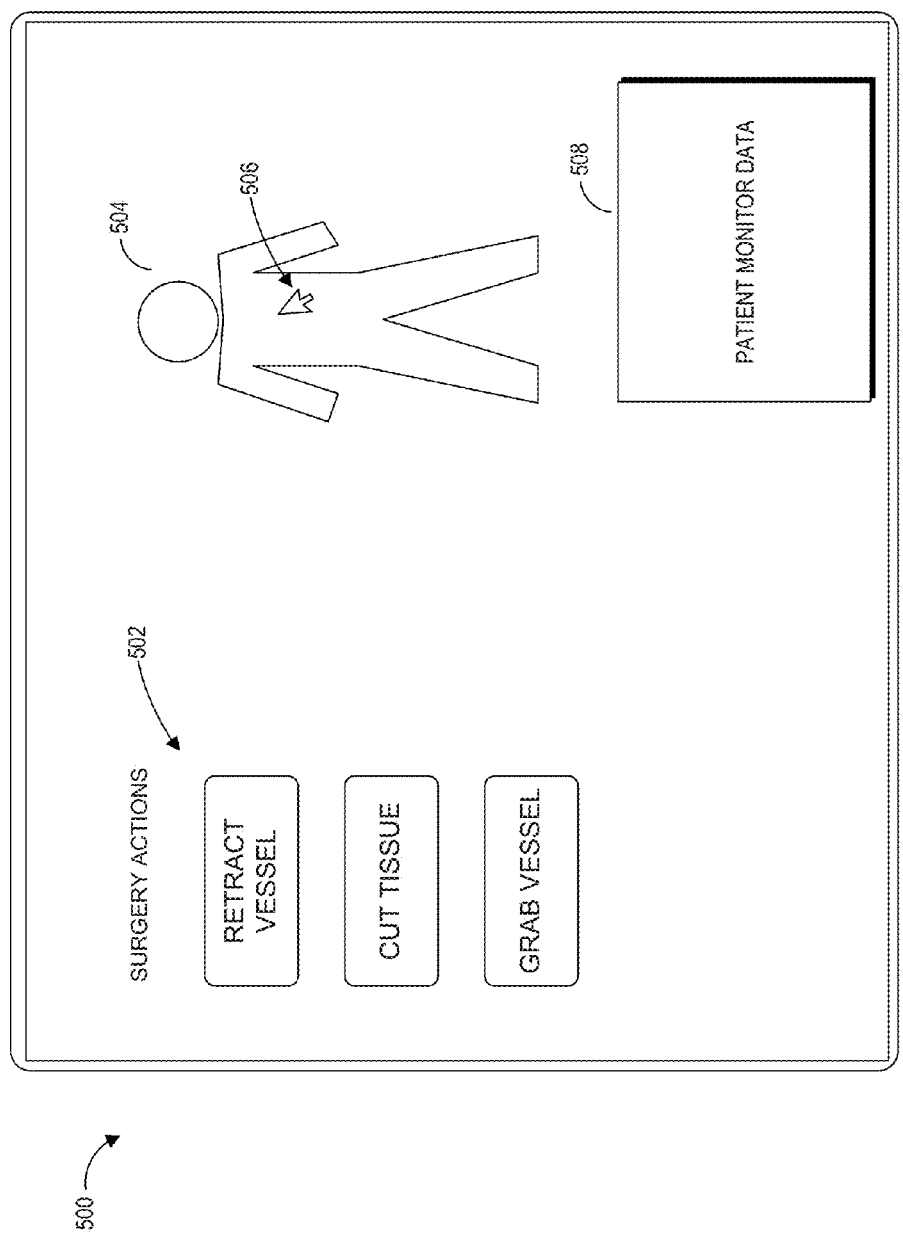
FIG. 5 illustrates an embodiment of a user interface for receiving proposed actions in a surgical environment.

FIGS. 4 and 5 illustrate example decision generator user interfaces 400 and 500 generated by a user interface module 118 of the decision generator system 110. More particularly, FIG. 4 illustrates a user interface 400 that can enable an operator to select a proposed action 404 for a decision request 402. The decision request 402 may be generated in response to a previous decision or may automatically appear based on an operator's specialty. For a UAV operator, the decision request 402 may be whether to launch a missile. The user interface module 118 can generate renditions of data and include them in the user interface 400. For example, the decision generator system 110 can receive data from satellites or other systems and include such data, possibly after transforming into a more readable version, in the user interfaces 400, 500. For example, the user interface module may convert satellite data to images showing the location of the target (e.g., an overhead map) and/or a picture of the target 410. The user interface module 118 can receive operator selection of one of the proposed actions 404. In some embodiments, the user interface module 118 can request a confidence level (not shown) of an operator in selecting a particular proposed action.

FIG. 5 illustrates a user interface 500 that can enable an operator (e.g. surgeon) to select a proposed action 502 while an execution system is operating on a patient 504. The user interface module 118 can generate a rendition of the patient and/or show a live video feed to aid the operator in providing the input. Surgeons can select a particular action using a cursor 506, hand gestures, voice commands, and/or any other input mechanisms. In one embodiment, different gestures are associated with different proposed actions. For example, a first action (e.g., "retract vessel") may be associated with a single finger swipe from right to left, a second action (e.g., "cut tissue") may be associated with a two finger swipe from right to left, a third action (e.g., "grab vessel") may be associated with a three finger swipe, and so on. In one embodiment, the particular gesture associated with selection of a particular proposed action may be indicated in an icon near the displayed proposed action, such as to the right of the proposed action buttons 502 in FIG. 5.

In one embodiment, the user interface module 118 can also transform patient monitoring data into one or more graphs 508 (and/or other visualizations) and show indicators of patient health. The user interface module 118 can receive selection of one or more proposed actions from operators provided via the user interface 500. In some embodiments, the user interface 500 may include mechanical structures (e.g. robotic arm, joystick, touchscreen, mouse, trackball, etc.) for receiving proposed actions. The decision generator system 110 can use the proposed action to generate an instruction for execution by an execution system, such as a surgical procedure that is automatically executed by a surgical device in response to determination of an instruction by the decision generator system. In some embodiments, the user interface module 118 may show proposed actions from other operators.

VII. Example Decision Generator Processes

Figure 6:
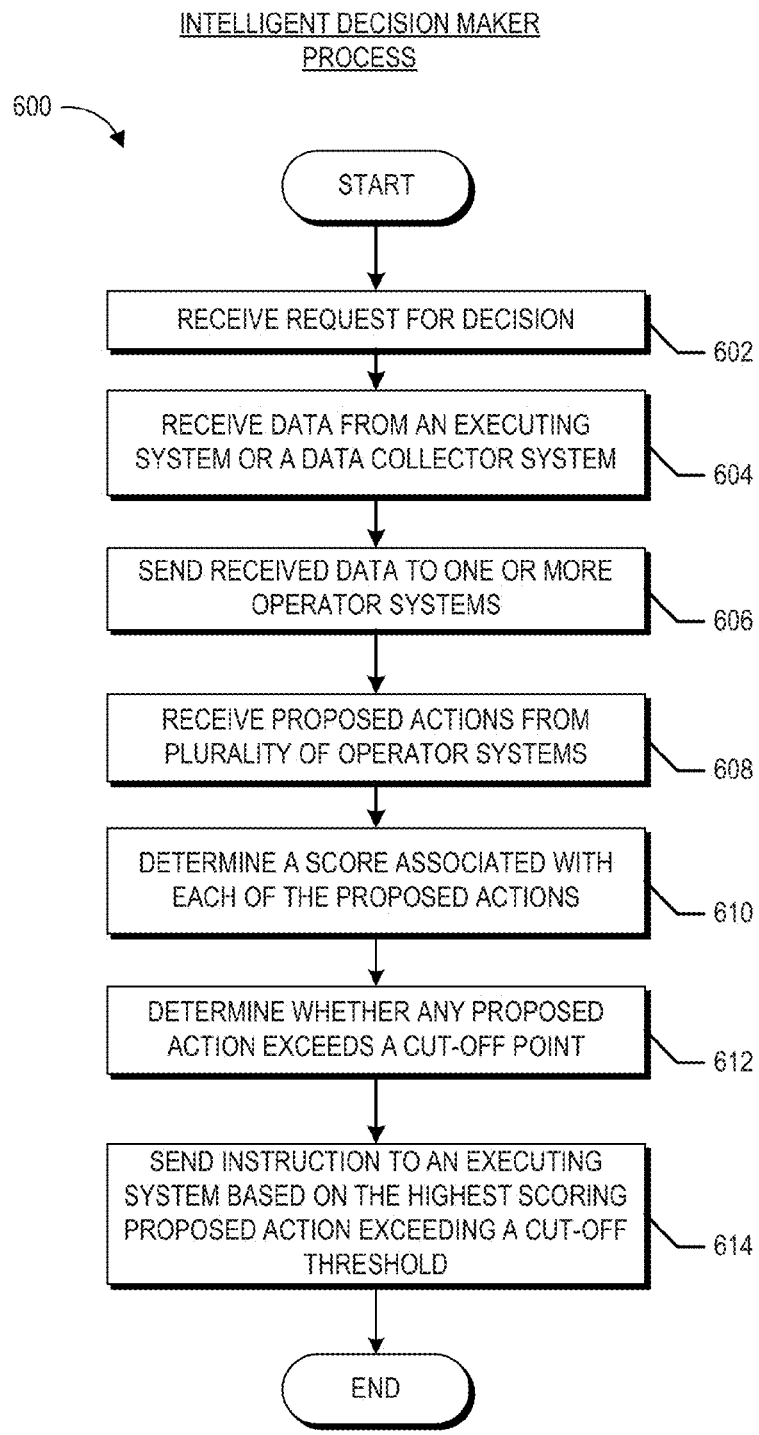
FIG. 6 illustrates an embodiment of an intelligent decision maker process.

FIG. 6 is a flowchart illustrating an embodiment of a decision maker process 600 for determining instructions for the execution system 122. The decision maker process 600 can be implemented by any of the systems described above. For illustrative purposes, the process 600 will be described as being implemented by a decision generator system 110. The process 600 depicts an example overview of decision generation process. Some of the details of the process are described above with respect to military and surgical embodiments; however, the process 600 is not limited to military or surgical embodiments and can be used in any other environments requiring intelligent decision making based on a plurality of inputs. Depending on the embodiment, the method of FIG. 6 may include fewer or additional blocks and the blocks may be performed in an order that is different than illustrated.

In some embodiments, the process 600 begins at block 602 where the decision generator system 110 receives a request for a decision to be made. Depending on embodiment, the request may come from various sources and in various manners. For example, in one embodiment a individual, such as an operator that is on-site to an environment associated with a decision may request that a decision be made by the decision generator system 110, such as by requesting a decision on a particular action via the user interface on a mobile device. In one embodiment, a decision request is generated automatically, such as by an execution system detecting a particular object, event, activity, etc. upon which one of multiple actions may be taken. For example, if an unmanned robotic vehicle execution system detects a convoy of vehicles in the direct planned travel route (e.g., based on computerized analysis of video images acquired by the vehicle), the execution system may transmit a decision request to the decision generator system 110. In some embodiments, the decision request includes the allowed proposed actions, such that operators may not provide any different proposed actions. Alternatively, a decision request may allow operators to provide additional proposed actions, such as using a "fill in the blank interface."

Moving to block 604, the decision generator system 110 may receive data from the executing system, one or more data collector systems, and/or other data sources. For example, in a military example, the decision generator system 110 may receive weather data regarding the event location from one or more data sources.

Next, at block 606, the decision generator system 110 can send the request for proposed actions in a user interface as described above and/or in any other format. The user interface module 118 can generate user interface data including proposed actions and transmit to one or more operator systems 108, supervisor system 122, and/or other system from which input regarding the decision is to be requested. Depending on the embodiment, the operators to which a decision request is transmitted may be determined in various manners. Example, in one embodiment a decision request (e.g., block 602) may include an indication of one or more groups of operators from which input is requested. In one embodiment, operators from which input is requested on a particular decision are automatically selected based on a type and/or content of a decision request. For example, a medical decision regarding a surgical procedure may be automatically transmitted to a first group of operators, while a medical decision regarding administering further anesthesia to a patient undergoing surgery may be automatically transmitted to a second group of operators (where the first and second groups of operators have no overlap, partial overlap, or entirely overlap in membership). In one embodiment, a decision request may be presented to a large group of operators and the operators can determine whether or not they individually would like to view further details regarding the decision request and provide a proposed action selection. For example, decision request associated with a surgical procedure may be shown in a user interface to each surgeon, and radiologist associated with the hospital, and any available surgeons or radiologists that would like to provide input regarding the surgical procedure may do so (e.g., with various weightings associated with the different operators based on their experience with the particular surgical procedure and/or other factors discussed above).

At block 608, the decision generator system 110 can receive one or more proposed actions from a plurality of operator systems 108 based on the operators' respective selection using the user interfaces. As noted above, in some embodiments the proposed actions may include additional information, such as confidence levels of respected reporters in the proposed action being selected.

Moving to block 610, the decision generator system 110 can generate scores associated with each of the proposed actions received from different operators. Some examples for generating scores are described above with respect to military and surgical environment.

Next, at block 612, the decision generator system 110 can determine if any of the proposed actions from the operator systems 108 exceed a cut-off point. As discussed above, various methods for aggregating, combining, or otherwise considering proposed actions from a plurality of operators may be implemented by the decision generator system 110. In one embodiment, the decision generator system 110 uses scoring methodology and thresholds for instruction generation based on the type of decision being requested. Thus, for a particular medical decision, scores from individual operator systems 108 may be combined in a first manner (e.g., averaging), while for a different medical decision, scores from individual operator systems 108 may be combined in a different manner (e.g., summing). Similarly, threshold scores for sending instructions to an execution system for automatic execution (e.g., without further input from any human operators) or execution after final approval from a human operator, may vary depending on the type of decision request. In some embodiments, the decision request may include indications of the scoring methodology and/or thresholds to be used in making the particular decision.

At block 614, the decision generator system 110 can send the proposed action with the highest score above a cut-off point (or with associated operator scores that otherwise cause selection of the proposed action) as instructions to an executing system 122.

Figure 7:
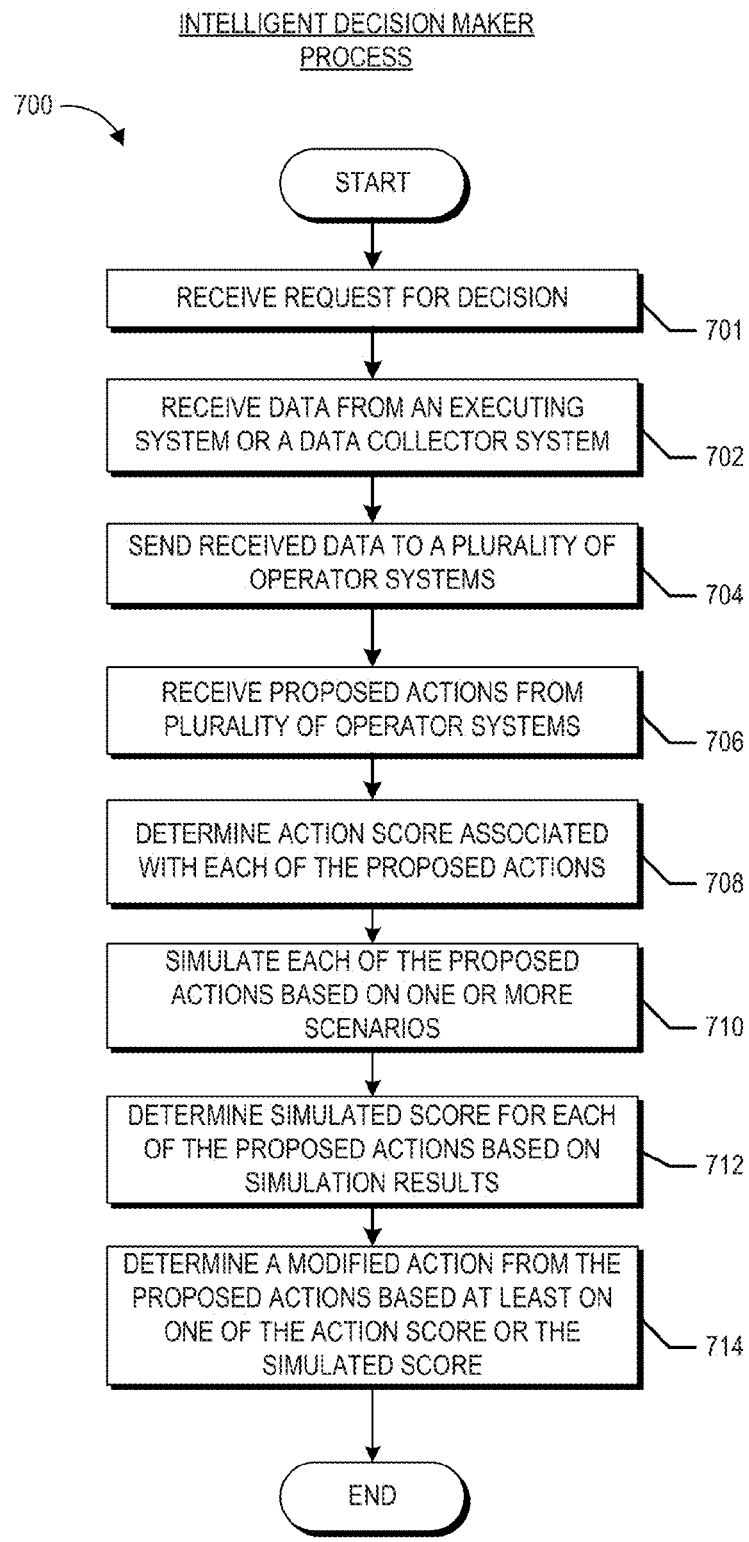
FIG. 7 illustrates an embodiment of an intelligent decision maker process.

FIG. 7 illustrates an embodiment of a decision maker process 600 for determining instructions for the execution system 122. The decision maker process 700 can be implemented by any of the systems described above. For illustrative purposes, the process 700 will be described as being implemented by the decision generator system 110. The process 700 depicts an example overview of decision generation process wherein the decision generator system 110 sends a modified proposed action to an execution system 122, as a replacement for or in addition to the proposed action. Moreover, the process 700 may also include simulating proposed actions in some embodiments as described above. Some of the details of the process were described above with respect to military and surgical embodiments; however, the process 700 is not limited to military or surgical embodiments and can be used in any other environments requiring intelligent decision making based on plurality of inputs. Depending on the embodiment, the method of FIG. 7 may include fewer or additional blocks and the blocks may be performed in an order that is different than illustrated.

In an embodiment, the process 700 can begin at block 701 where the decision generator system 110 receives a request for a decision to be made as described more in detail with respect to block 602 of FIG. 6. At block 702, the decision generator system 110 can receive data from one or more data collecting systems 124 and/or an executing system 122. The decision generator system 110 can send received data including some transformed data in a user interface to a plurality of operator systems 108 at block 704. Based on operator selection, the decision generator system 110 can receive proposed actions from the plurality of operator system 108. The decision generator system 110 can determine an action score associated with each of the proposed actions based on a first set of criteria at block 708. Examples of generating action scores are described above with respect to military and surgical environments. In some embodiments, the decision generator system 110 can simulate proposed actions at block 710 to improve decision making ability. The decision generator system 110 can simulate based on a plurality of scenarios and available condition data as discussed more in detail below. The decision generator system 110 can determine simulated scored based on simulation results from each of the proposed actions as described above. At block 714, the decision generator system 110 can accordingly select a modified action based on either the action score and/or simulated scores. In the example described with respect to a surgical environment, the decision generator system 110 can take a median of where to make a cut based on outcomes of multiple simulated cut locations. In another example, the decision generator system 110 can evaluate the probability of the target hit based on simulated results and send modified instructions to an executing system 122 accordingly.

VIII. Event Log

The decision generator system 110 can also generate an event log 800 in some embodiments, as illustrated in the example of FIG. 8. The user interface module 118 can generate a user interface that can display the event log 800 including a summary of decision making process for one or more events. In the depicted example, the event log includes a summary for a decision request of whether to fire a missile on the target shown? The decision request can be sent to multiple operators 1-4, such as using an interface similar to those shown with respect to FIGS. 4 and 5. The event log 800 further shows proposed actions received via each operator systems 108. In some embodiments, the timings of the responses and the calculated scores associate with each of the responses are also included in the event log 800. In this example, the decision generator system 110 selected the instruction to not fire the missile from Operator 3 because that proposed action had the highest score above the cutoff threshold of 50 for the particular scenario. As noted above, in some embodiments proposed actions are selected in different manners, such as based on aggregated scores from multiple operators. In the example of FIG. 8, the decision generator system 110 did not take into account the proposed action from Operator 4 because of the need to make a decision under a minute in this particular situation.

In some embodiments, information such as that shown in the event log of FIG. 8 may be provided to one or more operators in real time as decision request are transmitted to various operators and responses are received. Thus, responses from operators may appear (in real time) on such a user interface so that a viewer can see the various responses being received by the decision generator system 110. In this embodiment, the decision generator system may include a current recommendations/instruction to be provided to the execution system, based on the currently available input from operators. Thus, the viewer can watch the recommendations/instruction change over time as input from additional operators is received. In one embodiment, the viewer is a high-level official that is authorized to proceed with execution of an instruction suggested by the decision generator system 110 at any time. Thus, such a viewer may provide an input indicating that a currently displayed instruction be transmitted to the execution system, even before a decision time period is lapsed and/or responses from all operators is received.

IX. Implementation Mechanisms

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 9:
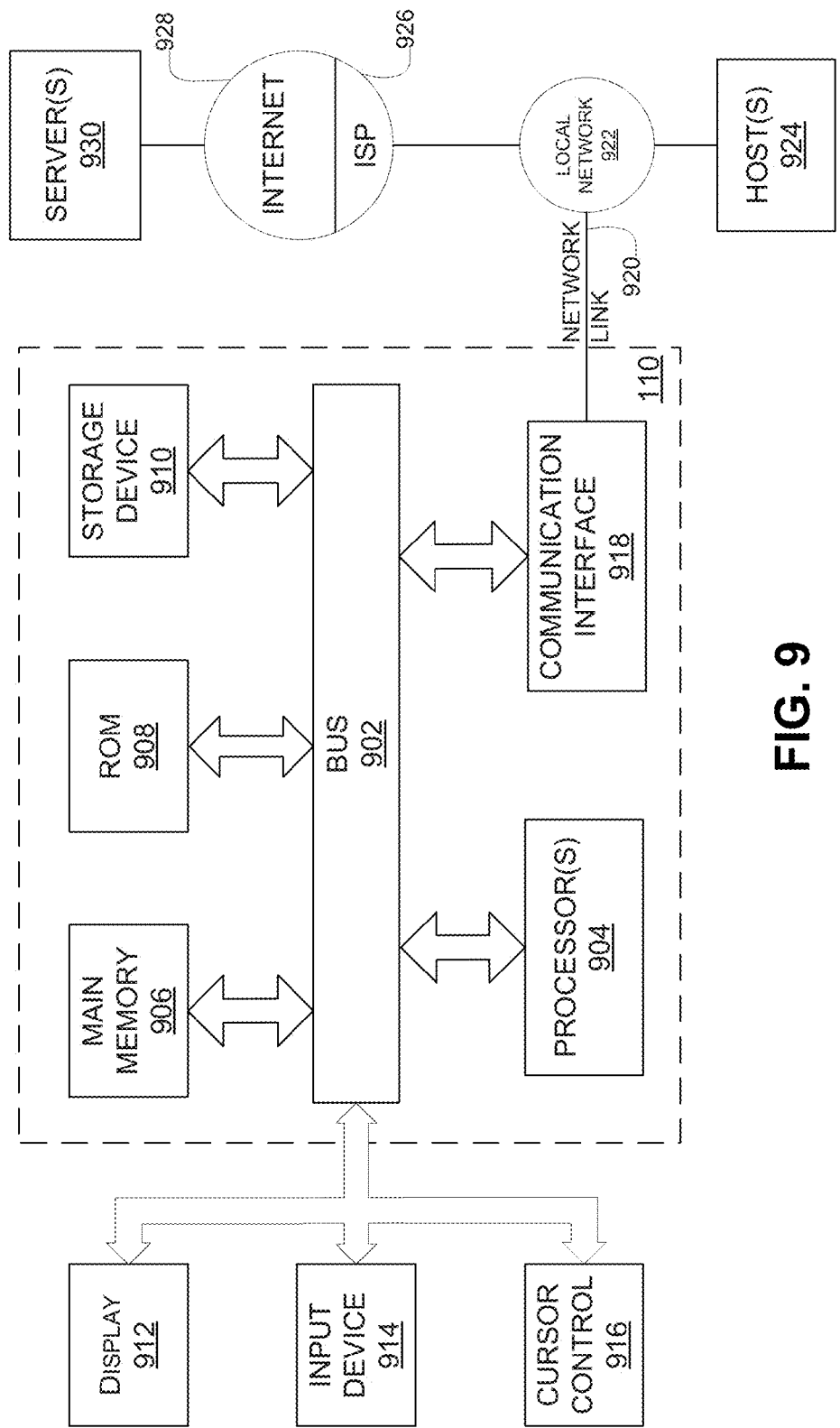
FIG. 9 is a block diagram that illustrates example components of the decision generator system.

For example, FIG. 9 is a block diagram that illustrates example components of the decision generator system 110. Any other computing devices or systems discussed herein may include some or all of the same or similar components as discussed with reference to FIG. 9.

The example computer system 900 includes a bus 902 or other communication mechanism for communicating information, and a hardware processor, or multiple processors, 904 coupled with bus 902 for processing information. Hardware processor(s) 904 may be, for example, one or more general purpose microprocessors.

Computer system 900 also includes a main memory 906, such as a random access memory (RAM), cache and/or other dynamic storage devices, coupled to bus 902 for storing information and instructions to be executed by processor 904. Main memory 906 also may be used for storing temporary variables or other intermediate information during execution of instructions to be executed by processor 904. Such instructions, when stored in storage media accessible to processor 904, render computer system 900 into a special-purpose machine that is customized to perform the operations specified in the instructions.

Computer system 900 further includes a read only memory (ROM) 908 or other static storage device coupled to bus 902 for storing static information and instructions for processor 904. A storage device 910, such as a magnetic disk, optical disk, or USB thumb drive (Flash drive), etc., is provided and coupled to bus 902 for storing information and instructions.

Computer system 900 may be coupled via bus 902 to a display 912, such as a cathode ray tube (CRT) or LCD display (or touch screen), for displaying information to a computer user. An input device 914, including alphanumeric and other keys, is coupled to bus 902 for communicating information and command selections to processor 904. Another type of user input device is cursor control 916, such as a mouse, a trackball, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 900 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage Computer system 900 may implement the techniques described herein using customized hard-wired logic, one or more ASICs or FPGAs, firmware and/or program logic which in combination with the computer system causes or programs computer system 900 to be a special-purpose machine. According to one embodiment, the techniques herein are performed by computer system 900 in response to processor(s) 904 executing one or more sequences of one or more instructions contained in main memory 906. Such instructions may be read into main memory 906 from another storage medium, such as storage device 910. Execution of the sequences of instructions contained in main memory 906 causes processor(s) 904 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 910. Volatile media includes dynamic memory, such as main memory 906. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise bus 902. Transmission media can also take the form of acoustic or light waves, such as those generated during radio-wave and infra-red data communications.

Various forms of media may be involved in carrying one or more sequences of one or more instructions to processor 904 for execution. For example, the instructions may initially be carried on a magnetic disk or solid state drive of a remote computer. The remote computer can load the instructions into its dynamic memory and send the instructions over a telephone line using a modem. A modem local to computer system 900 can receive the data on the telephone line and use an infra-red transmitter to convert the data to an infra-red signal. An infra-red detector can receive the data carried in the infra-red signal and appropriate circuitry can place the data on bus 902. Bus 902 carries the data to main memory 906, from which processor 904 retrieves and executes the instructions. The instructions received by main memory 906 may retrieves and executes the instructions. The instructions received by main memory 906 may optionally be stored on storage device 910 either before or after execution by processor 904.

Computer system 900 also includes a communication interface 918 coupled to bus 902. Communication interface 918 provides a two-way data communication coupling to a network link 920 that is connected to a local network 922. For example, communication interface 918 may be an integrated services digital network (ISDN) card, cable modem, satellite modem, or a modem to provide a data communication connection to a corresponding type of telephone line. As another example, communication interface 918 may be a local area network (LAN) card to provide a data communication connection to a compatible LAN (or WAN component to communicated with a WAN). Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to a host computer 924 or to data equipment operated by an Internet Service Provider (ISP) 926. ISP 926 in turn provides data communication services through the world wide packet data communication network now commonly referred to as the "Internet" 928. Local network 922 and Internet 928 both use electrical, electromagnetic or optical signals that carry digital data streams. The signals through the various networks and the signals on network link 920 and through communication interface 918, which carry the digital data to and from computer system 900, are example forms of transmission media.

Computer system 900 can send messages and receive data, including program code, through the network(s), network link 920 and communication interface 918. In the Internet example, a server 930 might transmit a requested code for an application program through Internet 928, ISP 926, local network 922 and communication interface 918.

The received code may be executed by processor 904 as it is received, and/or stored in storage device 910, or other non-volatile storage for later execution.

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

X. Terminology and Conclusion

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a" and "an" are to be construed to mean "one or more" or "at least one" unless specified otherwise.

Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

While the above detailed description has shown, described, and pointed out novel features as applied to various embodiments, it will be understood that various omissions, substitutions, and changes in the form and details of the devices or algorithms illustrated can be made without departing from the spirit of the disclosure. Thus, nothing in the foregoing description is intended to imply that any particular feature, characteristic, step, module, or block is necessary or indispensable. As will be recognized, the processes described herein can be embodied within a form that does not provide all of the features and benefits set forth herein, as some features can be used or practiced separately from others. The scope of protection is defined by the appended claims rather than by the foregoing description.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment. Accordingly, no feature or group of features is necessary or indispensable to each embodiment.

A number of applications, publications, and external documents may be incorporated by reference herein. Any conflict or contradiction between a statement in the body text of this specification and a statement in any of the incorporated documents is to be resolved in favor of the statement in the body text.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. A computer-implemented system for determining an instruction that can be executed by an executing system, the system comprising:
   one or more computer processors;
   a non-transitory computer-readable storage device storing instructions configured for execution by one or more computer processors in order to cause the system to:
   request proposed actions regarding an event from each of a plurality of human operators, each associated with a corresponding operator system;
   receive proposed actions from the plurality of operator systems, wherein the proposed actions are based at least on data corresponding to an environment associated with the event;
   for each operator system providing a proposed action, determine a weighting associated with the operator system based on one or more parameters of the operator systems, the parameters comprising one or more of a proximity of the operator system to an execution location or experience of a human operator associated with the particular operator system in making decisions regarding other events of a similar type to the event;
   calculate a score for each of the proposed actions received from the plurality of operator systems based on the respective determined weightings associated with the operator systems;
   determine, within a predetermined first time period from requesting the proposed actions, based on the calculated scores for the proposed actions received from the plurality of operator systems, said instruction configured to be executed by an executing system; and
   command the executing system to execute the instruction within the first time period that is based at least on one of the proposed actions received from the operator systems.

2. The system of claim 1, wherein the instruction to calculate a score for each of the proposed actions received from the plurality of operator systems comprises:
   simulate results for each of the proposed actions; and
   calculate a score based on the simulated results.

3. The system of claim 1, wherein the instructions are further configured to cause the system to select plurality of operator systems based on one or more parameters of the operator systems, the parameters comprising one or more of a proximity of the operator system to an execution location, experience of an operator associated with the particular operator system in making decisions regarding other events of a similar type to the event.

4. The system of claim 1, wherein the first time period comprises real time.

5. The system of claim 1, wherein the first time period is less than or equal to one minute.

6. The system of claim 1, wherein the environment associated with the event includes an operating room environment, said data corresponding to the environment associated with the event including patient data.

7. The system of claim 1, wherein the environment associated with the event includes a securities transaction environment, said data corresponding to the environment associated with the event including stock market data.

8. The system of claim 1, wherein the environment associated with the event includes a military environment, said data corresponding to the environment associated with the event including field data.

9. The system of claim 1, wherein the environment associated with the event includes a military environment, said data corresponding to the environment associated with the event including field data from a system on the field.

10. The system of claim 1, wherein the environment associated with the event includes a factory environment, said data corresponding to the environment associated with the event including machine data.

11. A method of determining an instruction that can be executed by an executing system, the method comprising:
- requesting proposed actions regarding an event from each of a plurality of human operators, each associated with a corresponding operator system;
- receiving proposed actions from the plurality of operator systems, wherein the proposed actions are based at least on data corresponding to an environment associated with the event;
- for each operator system providing a proposed action, determining a weighting associated with the operator system based on one or more parameters of the operator systems, the parameters comprising one or more of a proximity of the operator system to an execution location or experience of a human operator associated with the particular operator system in making decisions regarding other events of a similar type to the event;
- calculating, using one or more hardware processors, a score for each of the proposed actions received from the plurality of operator systems based on the respective determined weightings associated with the operator systems;
- determining, within a predetermined first time period from requesting the proposed actions, based on the calculated scores for the proposed actions received from the plurality of operator systems, said instruction configured to be executed by an executing system; and
- commanding the executing system to execute the instruction within the first time period that is based at least on one of the proposed actions received from the operator systems.

12. The method of claim 11, wherein calculating, using one or more hardware processors, a score for each of the proposed actions received from the plurality of operator systems comprises:
- simulating results, using one or more hardware processors, for each of the proposed actions; and
- calculating, using one or more hardware processors, a score based on the simulated results.

13. The method of claim 11, further comprising selecting plurality of operator systems based on one or more parameters of the operator systems, the parameters comprising one or more of a proximity of the operator system to an execution location, experience of an operator associated with the particular operator system in making decisions regarding other events of a similar type to the event.

14. The method of claim 11, wherein the first time period comprises real time.

15. The method of claim 11, wherein the first time period is less than or equal to one minute.

16. The method of claim 11, wherein the environment associated with the event includes an operating room environment, said data corresponding to the environment associated with the event including patient data.

17. The method of claim 11, wherein the environment associated with the event includes a securities transaction environment, said data corresponding to the environment associated with the event including stock market data.

18. The method of claim 11, wherein the environment associated with the event includes a military environment, said data corresponding to the environment associated with the event including field data.

19. The method of claim 11, wherein the environment associated with the event includes a factory environment, said data corresponding to the environment associated with the event including machine data.

20. A non-transitory computer readable storage storing instructions configured to cause a computing system having a computer processor to:
- request proposed actions regarding an event from each of a plurality of human operators, each associated with a corresponding operator system;
- receive proposed actions from the plurality of operator systems, wherein the proposed actions are based at least on data corresponding to an environment associated with the event;
- for each operator system providing a proposed action, determine a weighting associated with the operator system based on one or more parameters of the operator systems, the parameters comprising one or more of a proximity of the operator system to an execution location or experience of a human operator associated with the particular operator system in making decisions regarding other events of a similar type to the event;
- calculate a score for each of the proposed actions received from the plurality of operator systems based on the respective determined weightings associated with the operator systems;
- determine, within a predetermined first time period from requesting the proposed actions, based on the calculated scores for the proposed actions received from the plurality of operator systems, said instruction configured to be executed by an executing system; and
- command the executing system to execute the instruction within the first time period that is based at least on one of the proposed actions received from the operator systems.

* * * * *